United States Patent [19]

Lau et al.

[11] Patent Number: 5,060,516
[45] Date of Patent: Oct. 29, 1991

[54] METHOD AND APPARATUS FOR NON-DESTRUCTIVE TESTING THE QUALITY OF MANUFACTURING WOOD PANELS

[75] Inventors: Peter W. Lau, Gloucester; Yvon G. Tardif, Gatineau, both of Canada

[73] Assignee: Forintek Canada Corp., Ottawa, Canada

[21] Appl. No.: 588,860

[22] Filed: Sep. 27, 1990

[30] Foreign Application Priority Data

Sep. 29, 1989 [CA] Canada .................................. 614463

[51] Int. Cl.⁵ ............................................. G01M 7/00
[52] U.S. Cl. ........................................ 73/602; 73/579; 73/580; 73/650
[58] Field of Search ................... 73/579, 580, 602, 650

[56] References Cited

U.S. PATENT DOCUMENTS

| | | | |
|---|---|---|---|
| 3,786,673 | 1/1974 | Weissman | 73/579 |
| 3,903,734 | 9/1975 | Douglas | 73/579 |
| 4,342,229 | 8/1982 | Massa | 73/579 |
| 4,722,223 | 2/1988 | Bach et al. | 73/579 |

*Primary Examiner*—Tom Noland
*Assistant Examiner*—W. Francos
*Attorney, Agent, or Firm*—Stanley E. Johnson

[57] ABSTRACT

Method and apparatus for non-destructive testing the quality of manufactured wood panels which includes supporting the panel so as to have a portion thereof in cantilevered fashion. The cantilevered portion of the panel is caused to vibrate so as to include complex vibrations that include both twisting and bending. The vibrations in the panel are sensed providing an output signal that is fed to analyzers and computers to determine from the simultaneously induced bending and twisting vibrations respectively the modulus of elasticity and shear modulus of the panel. Two different forms of apparatus are illustrated, one of which requires the panel to be stationary while being tested and the other in which the panel moves continuously while vibrations are induced and the induced vibrations sensed. The apparatus includes a weigh station to weigh the panel, apparatus to determine the thickness of the panel, apparatus to induce a vibration in the panel and apparatus to clamp the panel so as to have a portion cantilevered therefrom. In one apparatus the panel passes through a variable sized window opening that in the opened position receives the panel endwise and in the closed position, clamps the panel, holding it still while vibrations are induced in the panel. In the second apparatus, the clamping mechanism is a pair of counter-rotating cooperating endless belts, engaging respectively an upper and lower face of the panel.

19 Claims, 4 Drawing Sheets

METHOD AND APPARATUS FOR NON-DESTRUCTIVE TESTING THE QUALITY OF MANUFACTURING WOOD PANELS

FIELD OF THE INVENTION

This invention relates generally to a method and apparatus for checking the quality of manufactured wood panels by analyzing complex vibrations induced in the panel.

BACKGROUND OF INVENTION

In Canada and the U.S., wood based panel products are manufactured to comply with the requirements of product or performance standards such as those of the CSA and ASTM. This does not, however, preclude some variability in the product properties within a mill or between mills. The mills are responsible for the quality of their own products and their continued compliance with the standard. Existing quality control is based on small specimen bending and internal bond destructive tests which make for extremely slow feed-back. Since the test results are used for both quality and process control, it is of utmost interest to reduce the lag time.

A type of known non-destructive testing is based on established vibration theory, making use of measured thickness, weight and frequency of vibration. The vibration testing of lumber is known using complex vibrations of bending and twisting. A rectangular piece of lumber for example, a 241 ×4", 2"×6", 2"×8" or 2"×10", etc., can be tapped at an eccentric position such as along its edge and this produces, in the piece of lumber, complex vibrations of bending and twisting. The bending vibration and the twisting vibrations occur independently because the beams cross is rectangular. It is known that this vibration provides a means of nondestructive evaluation enabling the prediction simultaneously of the modulus of elasticity and the shear modulus. An article entitled "Simultaneous Determination of Young's Modulus and Shear Modulus of Structural Lumber by Complex Vibrations of Bending and Twisting" by Nobuo Sobue was published in Mokuzai Gakkaishi, Volume 34, Number 8, Pages 652 to 657 (1988).

The vibration theory concept has been used for establishing a measure of the modulus of elasticity of a wood panel as disclosed in U.S. Pat. No. 4,722,223 issued Feb. 2, 1988 to Lars Bach et al. Pure bending vibration on the panel product is produced by transversely impacting the panel along its central axis while it is supported flat-wise on a three point support system. A single sensor is used to detect the resonant frequency of bending vibration which is used, along with the panel weight and dimensions, to calculate the dynamic modulus of elasticity.

In the aforementioned U.S. Pat. No. 4,722,223, dealing with vibration testing of panel products, the method of panel support restricts the measurement to a single panel property, namely the modulus of elasticity, from the single impact that produces panel vibration. The prior art concerning complex bending and torsional vibrations and the theory applicable to torsional vibration are known to be applicable to rod like materials of circular or rectangular cross section, but it has not been known to be applicable to plate-like panel products. Also it should be pointed out that the combined torsion and bending technique in the prior art requires multiple impacts and sensors to generate, capture and separate the two types of vibration signals.

SUMMARY OF INVENTION

This invention relates to a method and apparatus for non-destructively determining, from simultaneous bending and torsional vibrations, in wood based panel products, the modulus of elasticity (MOE) in bending (flexure) and the modulus of rigidity (G) (shear modulus) for the purpose of quality control and/or grading.

The apparatus of the present invention provides fast feed-back and in the mill can be operating on-line thereby improving quality control.

In accordance with one aspect of the present invention there is provided a non-destructive method of testing the quality of a manufactured panel made of wood products comprising:
 a) supporting the panel in such a manner as to have a portion thereof projecting beyond the support and thereby providing an unsupported panel portion;
 b) causing complex vibrations in said unsupported portion of the panel so as to include both twisting and bending vibrations;
 c) sensing said complex vibrations and providing an output signal as a result thereof; and
 d) analyzing, from said output signal, each of the bending and twisting vibrations simultaneously induced into the panel and therefrom providing an indication of the quality of the panel by virtue respectively from an indication of its modulus of elasticity and shear modulus.

In accordance with another aspect of the present invention there is provided apparatus for non-destructive testing the quality of manufactured panels made of wood products comprising:
 a) a frame having an open window area into and through which a panel can be fed endwise;
 b) a beam extending along an edge of said window area, said beam providing a clamping base that has a substantially smaller panel engaging area than the major surface area of the panel to be tested;
 c) bar-like means for clampingly pressing a panel against said beam; and
 d) means located in selected spaced relation with respect to said beam, and at a position off-set from an axis of symmetry of a portion of a panel projecting in cantilever fashion from the beam, for detecting complex vibrations induced in the cantilevered portion of the panel, said vibrations including both bending and torsional vibrations that, when analyzed, provide an indication of the quality of the panel.

LIST OF DRAWINGS

The invention is illustrated by way of example with reference to the accompanying drawings wherein:

FIG. 4 is a typical frequency spectrum of the simultaneous torsion and bending frequency obtained for the complex vibration time signal of FIG. 5;

DETAILED DESCRIPTION OF PREFERRED EMBODIMENTS

Figure 1:
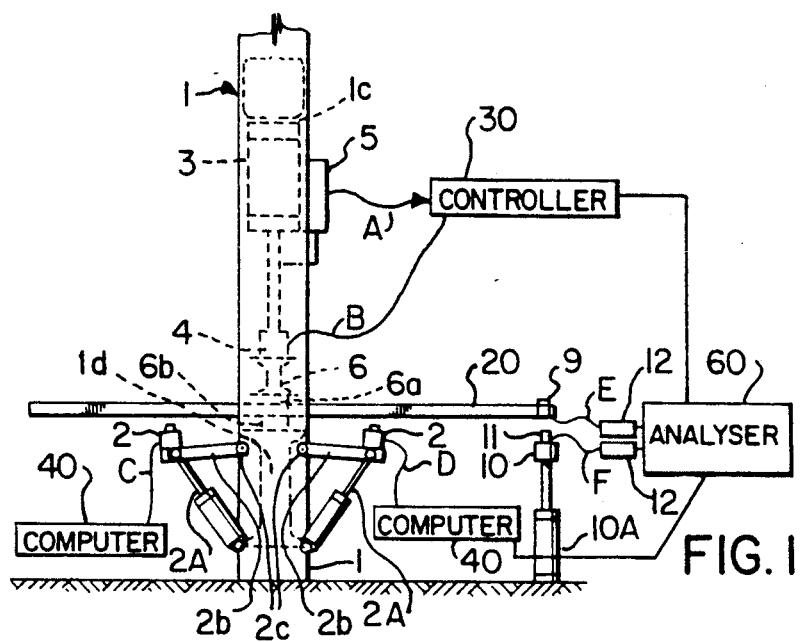
FIG. 1 is a diagrammatic side-elevational view of an apparatus provided in accordance with the present invention.
Figure 2:
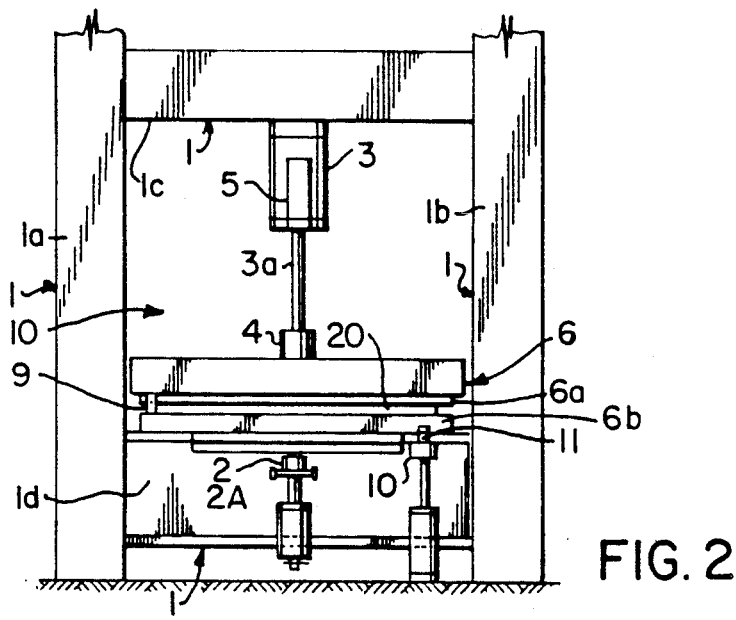
FIG. 2 is a right hand elevational view of FIG. 1.
Figure 3:
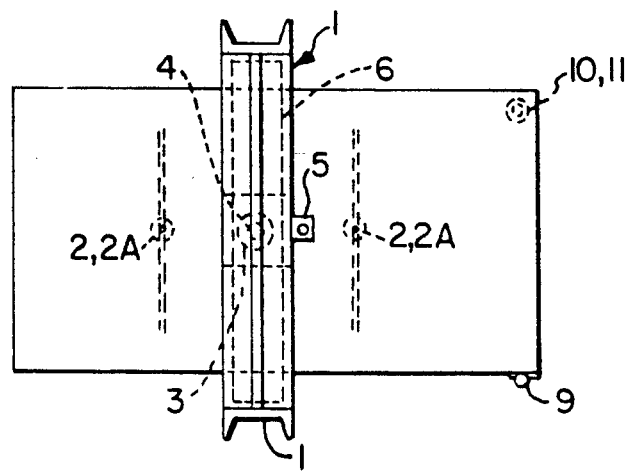
FIG. 3 is a top plan view of FIG. 1.

There is illustrated in FIGS. 1, 2 and 3 apparatus provided by the present invention for testing specimens or full size panels as a means to indicate the quality of wood based panel products such as plywood, waferboard, particle board, oriental strained board and the like. The apparatus is adapted for on-line quality control because panels to be tested can be readily moved endwise into and out of the test apparatus.

Referring to FIGS. 1 to 3, the apparatus includes a rigid frame 1 that includes vertical, horizontally spaced apart posts 1a and 1b interconnected by vertically spaced apart respectively upper and lower crossbeams 1c and 1d. The frame 1 is effectively a weldment of members around the periphery of an area designated 10. Part of the area 10 has what might be considered a variable in size window opening for receiving and clamping therein the panel 20 to be tested. The variable in size window area is defined by the lower cross-beam 1d and a movably mounted transverse I beam 6. Depending from the underside of this I beam 6, is a pillow block 6a that extends longitudinally along the beam for engaging the top surface of the panel 20 to be tested. A similar pillow block 6b is located on the upper surface of the lower cross-beam 1d. The panel 20 is clamped between the pillow blocks 6a and 6b and the space between such blocks is effectively a window with a variable size opening for receiving and clamping therebetween the panel to be tested.

The cross-beam 6 is effectively a load spreader and is suspended by a hydraulic cylinder unit 3 from the top cross-beam 1c of the frame. Interposed in the hydraulic clamping mechanism, between the cross-beam 6 and the cylinder 3, is a load cell 4. A displacement transducer 5 measures movement of the piston rod 3a of the hydraulic cylinder unit 3. The load cell 4 measures the clamping force which is distributed evenly across the width of the panel by the load spreader or transverse beam 6. The displacement transducer 5 measures the thickness of the panel. Signals from the transducers 4 and 5 (designated respectively A and B in FIG. 1) are fed to a controller 30.

The panel support frame 1 has a panel weighing system, mounted thereon, consisting of two load cells 2 mounted on respective ones of a pair of arms 2b. The arms are pivoted as at 2c on the lower cross-beam 1d and are selectively movable by respective ones of a pair of hydraulic cylinder jack units 2a. Movement of the arms 2b bring the load cells into and out of engagement with the underside of the panel 20 resting on pillow block 6b. The arms can be pivoted to the extent that the panel is lifted or raised off the pillowblock 6b. Signals from the load cells 2 are fed via respective lines C and D to a computer 40 which computes the weight of the panel.

The panel being tested projects in cantilever fashion from opposite sides of the clamping mechanism which consists of the relatively movable beams 1d and 6. A vibration sensor 9, which may be a contact or a non-contact type, is located at one outer free corner of the cantilevered portion of the panel and an impact device 10, having a force sensing transducer 11, is located near the opposite corner of the same cantilevered portion. The impact device 10 and vibration detector 9 are located respectively on opposite sides of the center line of the projecting portion of the panel. The vibration sensor 9 may be of the type attached to the corner of the panel and simultaneously detects both torsional and bending vibrations. The impact device 10, with the force sensing transducer 11, is located under a corner of the cantilevered portion of the panel to impart to it bending and torsional vibrations. The impact hammer is operated by a pneumatic, or the like, hydraulic cylinder unit 10a. Signals from the vibration sensor 9 and force sensing transducer 11 (designated respectively E and F) are sent to an analyzer 60. Charge amplifiers 12 are used to amplify the low level vibration and impact force signals. The analyzer 60 is a dual channel spectrum analyzer that performs a spectra-analysis of the complex vibration signal to identify, quantify and qualify the bending and torsional vibration with respect to the frequency domain. The computer 40 processes the measured parameters and yields the dynamic modulus of elasticity in bending and the dynamic shear modulus in torsion based on theoretical equations.

Testing of wood based panels, with the foregoing apparatus, begins by placing a test panel on the weighing platform of the panel support frame such that the desired test span extends in cantilever fashion beyond the testing frame. It will be readily apparent the window defined by the vertical beams 1a and the relatively movable beams 6 and 1d is open to receive the test panel which can be propelled endwise on a conveyor system on-line in a mill or off-set from the manufacturing line so as to test selected panels in the production as may be desired. The weight of the panel is measured by the pair of load cells after which the weighing platform is retracted. The beam 6 is then lowered by the hydraulic jack 3 onto the panel's surface and the average panel thickness is recorded based on a signal from the displacement transducer 5 when the clamping pressure, from the force transducer 4, just begins to increase. The vibration sensor 9, which is an accelerometer, is attached to the corner of the cantilevered panel and captures vibrations in the panel while the impact device is positioned under the same or opposite corner. As previously described, the impact device is located under one corner while the sensor is under the opposite, but this need not be so as they both can be located under the same corner. What is important is that they both be off-set laterally from the central axis of the panel that is transverse to the clamping of the panel.

Upon activation the impact device delivers a single sharp blow to the underside of the panel causing, because of its eccentric location with respect to the central axis of the cantilevered span of the panel, a complex torsional and bending vibration. The impact load sensed by the load measuring transducer, of the impact device, triggers the acquisition of the complex vibration signal of the accelerometer 9 by the spectrum analyzer 60. The spectrum analysis reveals the frequency of both the torsion and bending vibrations which are comprised within the same spectrum. Although spectrum analysis was chosen as the technique of signal analysis, it does not exclude other signal processing and analysis techniques as a means of determining the frequency of each vibration of interest. For example, band pass filters may be used that are selectively tuned to the frequencies of concern. After the filtering process period averaging can be used for determining the frequencies. The measured torsion and bending frequencies are fed into the computer 40 and along with the panel weight and thickness, and processed to yield the modulus of elasticity in bending and the shear modulus of the panel for the span tested.

From the known theories of vibration in materials, the dynamic modulus of elasticity in bending of panel products can be computed from the resonant frequency of bending vibration using the following equation:

$$E\alpha = (4\pi^2 f^2 L^3/3I)(M + 33M_o/140)K$$

where
- $E\alpha$ = dynamic modulus of elasticity;
- f = frequency of resonance in bending;
- L = span over which the vibration are measured;
- M = mass attached to the end of the panel;
- $M_o$ = mass of portion of panel in vibration;
- K = constant for the gravitational units used; and
- I = $ab^3/12$ where
- a = width of the panel;
- b = thickness of the panel.

This equation is for the end-loaded free-fixed mode of vibration, where the test specimen is supported such that the tested span is in cantilever. This method of support is preferred to others to overcome problems with bow and twist in panels as reported in the prior art, and to fulfill the substance of the present invention. An endloaded cantilever condition is considered to allow for the mass of contact type vibration sensors to be compensated for in the calculation of the dynamic bending modulus when small panel sections are tested, where the mass of the sensor would significantly affect the vibration frequency.

In the case of torsional vibrations, the known vibration theory on rods indicates that the frequency of resonance in rod of circular or rectangular cross section can be used to predict the shear modulus using the following equation:

$$G_1 = 4\pi^2 f^2 I_o L / K_2 bd^3 \times 10^{-6}$$

where
- f = frequency of torsional vibration, Hz,
- L = span of panel, mm,
- b = width of panel, mm,
- d = thickness of panel, mm,
- $K_2$ = constant, and $I_o$ is the effective inertia mass of the system, in g-mm². It is normally assumed that one-third of the specimen inertia mass is concentrated at the free end, therefore, $$I_o = \beta PLbd^3/12$$

where $\beta$ = fraction of inertia mass assumed concentrated at end of cantilever, in this case $\frac{1}{3}$; and P = density of panel, g/mm³. The value of $K_2$ depends on the value of $$b/d(G_2/G_1)^{\frac{1}{2}}$$

where $G_2$ = modulus of rigidity in the plane perpendicular to that of G', i.e., in interlaminar shear.

In actual tests conducted, test samples of 400 specimens measuring 450 mm × 610 mm were cut from 15.9 mm waferboard panels representative of random and oriented Half of the specimens were obtained with their longest dimension running along the panel length and half with their longest dimension running across the panel length. The bending and torsion properties for comparison were obtained respectively from the results of tests carried out in accordance with the standard test method of ASTM D3043 C pure moment test for large panels, and ASTM D3044 test for determining the shear modulus of plywood. The pure moment tests were done on 610 mm by 1190 mm specimens cut from the same waferboard panels used for the preparation of the test specimens. The shear tests on the other hand were carried out on 610 mm by 610 mm specimens from which the test specimens were extracted. A static bending test was also conducted on the test specimens over the cantilevered span used in vibration testing to establish their respective bending MOE. In this latter case the following formula was used to compute the MOE:

$$MOE = 2Pa^2(3L-a)/\delta bd^3$$

where
- P = applied load;
- a = distance of applied load to fixed support, mm;
- L = length of cantilever, mm;
- $\delta$ = deflection at end of cantilever, mm;
- b = width of the panel, mm;
- d = thickness of the panel, mm.

Since the tests were carried out on small size panels, the mass of the accelerometer used for sensing the complex vibration had to be accounted for in the calculations of the dynamic bending and torsion properties. In addition the mass of the accelerometer needed to be counterbalanced to off-set its influence on the torsion frequency.

Computation of the dynamic modulus of elasticity from the bending frequency measured by the test was done using the forementioned equation from the vibration theory. The mass of the portion of the panel in vibration ($M_o$) was taken as the total mass of the panel under test multiplied by the ratio of the test span and the panel length. The value of the mass attached to panel (M), which is the combined mass of the accelerometer and counterweight, was adjusted according to the ratio of the sensor distance along the test span and the length of the test span. In dealing with the computation of the torsional property of panels from the torsion frequency of vibration a value of $K_2 = 0.3$ and a value of $\beta = 0.238$ were used. The former was obtained from the literature, while the latter was determined experimentally from separate tests. The value of $\beta$ will vary somewhat depending on specimen geometry and it may be necessary to make experimental determinations if better prediction of the static values is required.

Figure 4:
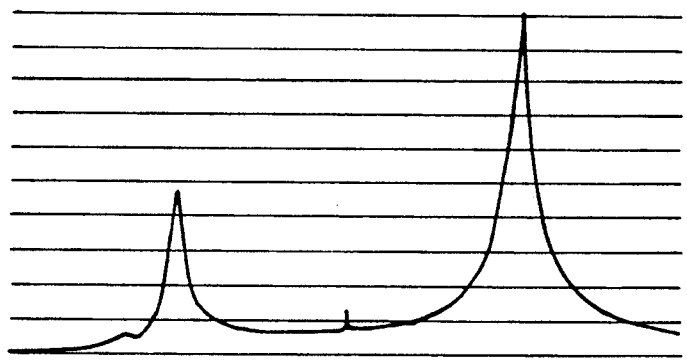
FIGS. 4 and 5 are graphs, where
Figure 5:
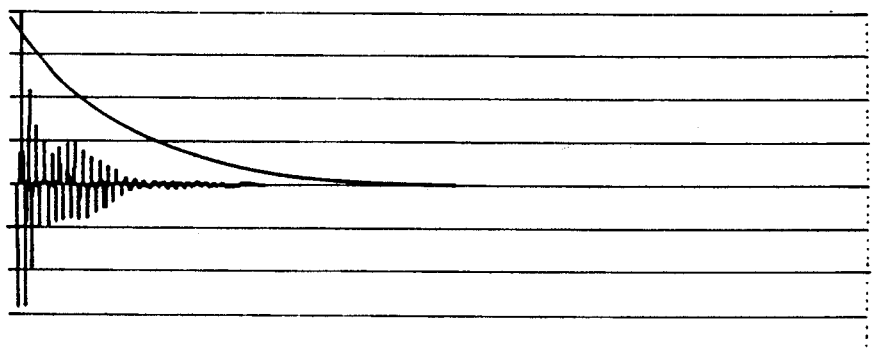

FIG. 4 shows a typical frequency spectrum of the simultaneous torsion and bending frequency obtained for the complex vibration time signal of FIG. 5. The lower frequency and lower amplitude peak corresponds to bending vibrations while the higher frequency and higher amplitude peak corresponds to the torsional vibrations.

Figure 6:
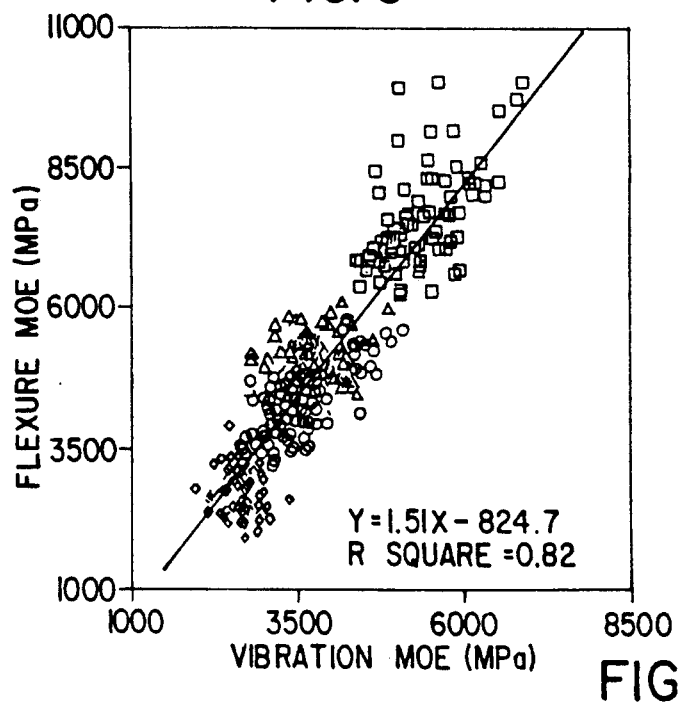
FIG. 6 is a graph illustrating the relationship between the modulus of elasticity (MOE) determined from flexure tests v. The dynamic MOE determined from tests using apparatus of the present invention.
Figure 7:
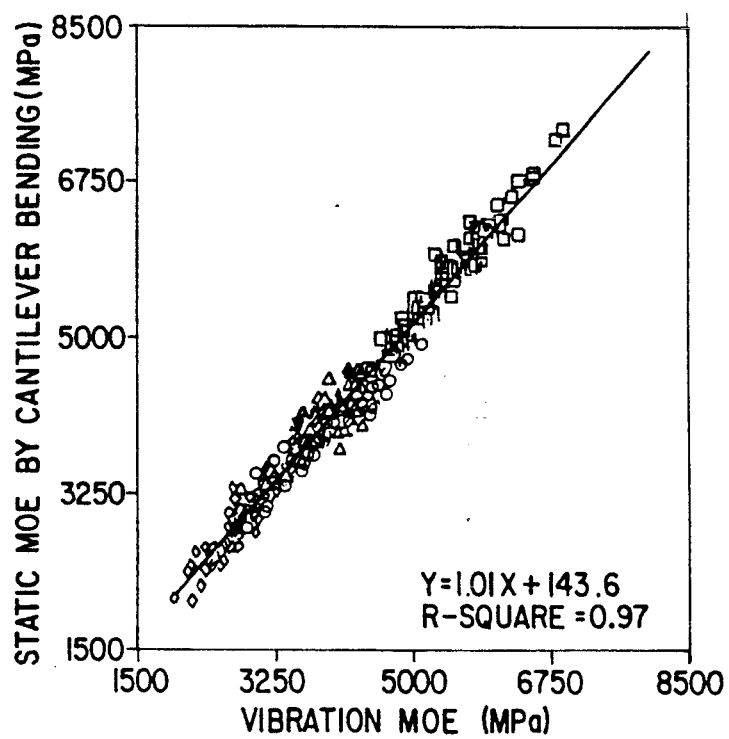
FIG. 7 is a graph illustrating the relationship between the MOE determined from the static bending tests on a cantilevered portion of the test specimen, using the present apparatus and the dynamic MOE.
Figure 8:
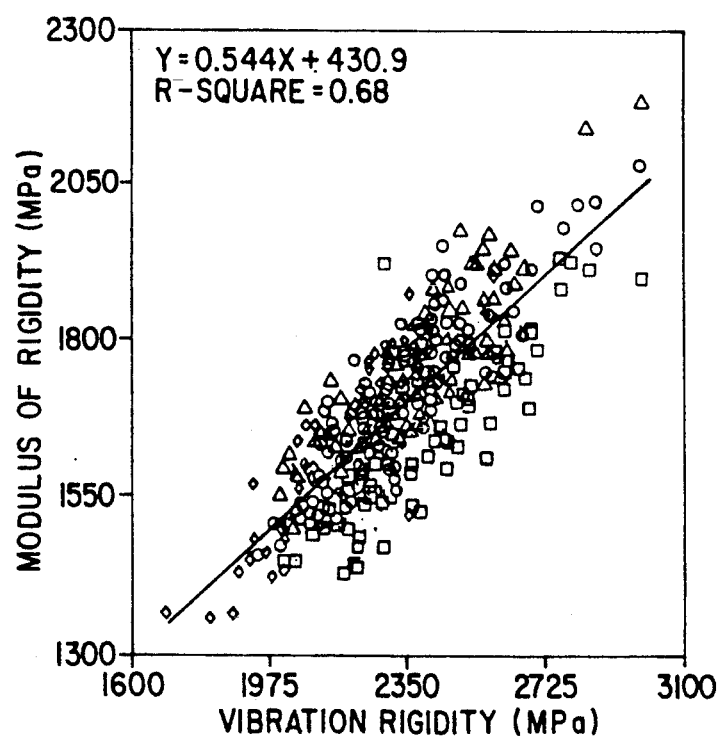
FIG. 8 is a graph illustrating the relationship between the modulus of rigidity from static tests and the modulus of rigidity in torsion from tests using apparatus of the present invention.

FIG. 6 presents the relationship between the MOE determined from the flexure tests and the dynamic MOE from the tests, regardless of the type of waferboard panel and the orientation of the test panel within the original full size panel. The high correlation obtained as evidenced by the $R^2$ of 0.82 is a clear indication that the dynamic MOE from the simultaneous torsion and bending vibration is a good predictor of the bending MOE of panels such as determined by conventional means; and this even when the latter is measured on different test specimens taken from the same sample group of panels. FIG. 7 shows the relationship between the MOE determined from the static bending tests on the cantilevered test specimens and the dynamic MOE from the test. The improved correlation between the static and dynamic properties ($R^2=0.97$) is attributable to the fact that both were determined on the same test panels and over the same test span: a further indication that the test dynamic MOE is a good predictor of its static counterpart. The relationship between the modulus of rigidity from the static tests and the modulus of rigidity in torsion from the tests is presented in FIG. 8. This relationship applies to all test panels without distinction to panel type or test specimen orientation. Although a lower correlation was obtained for this relationship ($R^2=0.68$) than for the previous one on the panel bending property, the dynamic shear modulus as determined from the torsion vibration of the test is a good predictor of the modulus of rigidity in panel products. This relationship would no doubt be enhanced along the same line as the improvement observed for the bending properties if both the static and vibration test procedures were carried out over the same test span.

From the foregoing, it can be seen there is provided a simple apparatus and a robust apparatus that can be readily positioned off to one side or on-line in a mill to test panels or selected panels as they are manufactured to give fast feed-back as to the quality of panels being produced. The apparatus, in simple terms, is a clamping mechanism for clamping the panel intermediate the end so as to have a portion of the panel cantilevered therefrom and which portion is caused to vibrate. The complex vibrations induced are analyzed providing respectively an indication of the modulus of shear and modulus of elasticity. The weigh mechanism illustrated in the foregoing and described as being part of the apparatus could be upstream from the apparatus. The weigh apparatus for example, may be a weigh table on the infeed side of the clamping mechanism such that the panel is weighed before being propelled endwise into the clamping mechanism.

The apparatus illustrated in FIGS. 1 to 3 requires holding the panel in a stationary position while weighing the panel, inducing vibrations in the cantilevered portion and detecting those induced vibrations. The intermittent movement in a mill flow manufacturing process can, if completely on-line, slow up the system. There is diagrammatically illustrated in FIGS. 9 and 10, a system for testing while the panels move in a continuous flow along a predetermined path, which may be on-line in the manufacturing without affecting the rate of production.

Figure 9:
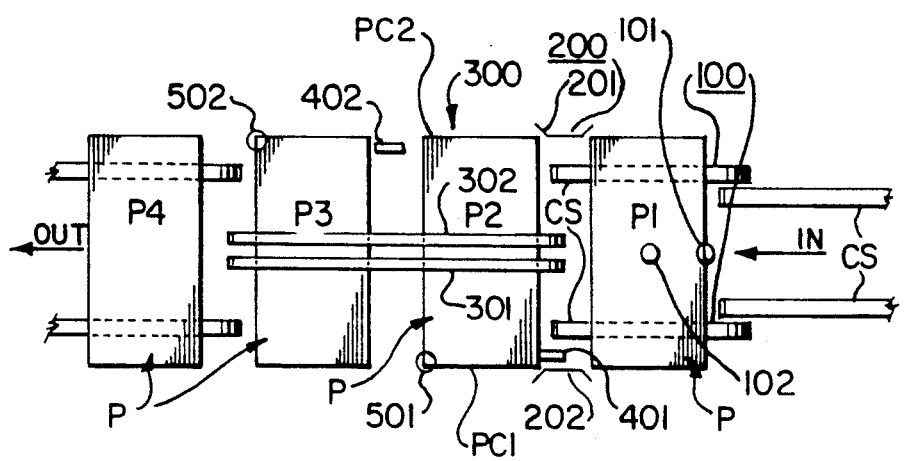
FIG. 9 is top plan diagrammatic view of apparatus for testing/panels in a continuous flow.
Figure 10:
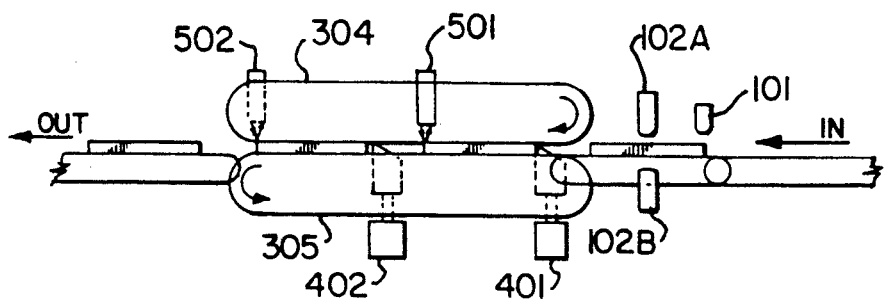
FIG. 10 is a side elevational diagrammatic view of FIG. 9.

Referring to FIG. 9, there is illustrated one panel P at four different positions designated respectively P1, P2, P3 and P4, downstream from one another in a continuous flow path in the direction of the in-out arrows, as the panel is conveyed by a conveyor system CS. The conveyor system CS, at panel position Pl, is isolated from the remaining part of the conveyor system and includes means for weighing the panel and constitutes a panel weighing station 100. At the infeed side of the weighing station 100, there is an infrared panel temperature sensing means 101. Also at the weighing station 100 there is located panel thickness measuring means 102, consisting of a pair of optical thickness gages 102A and 102B located respectively above and below the panel. As the panel moves in the direction of the arrows, from the weigh station 100, it passes through a guide system 200 that aligns the panel along a predetermined path. The guide system is diagrammatically illustrated as a pair of lateral guide members 201 and 202, that may be suitably positioned plates or alternatively endless belts or rollers that engage respectively opposite ends of the panel. The panel, as it continues, next enters a panel clamping station 300 which includes a first pair of rotary clamps 301 and a second pair of rotary clamps 302, laterally spaced apart from one another, equi-distantly from the center line of the panel that is moving along the selected path. Each of the pair of rotary clamps 301 and 302 have an upper endless belt member 304 and a lower endless belt member 305, rotating in opposite directions, as indicated by the arrows in FIG. 10. The upper and lower endless belt members 304 and 305 can be driven by any suitable power means to propel the panels while at the same time clamping a panel so as to provide cantilevered respective portions PC1 and PC2 as indicated in FIG. 9. The cantilevered portion PC1 is caused to vibrate by a vibration inducing mechanism 401 and the opposite cantilevered portion PC2 is caused to vibrate by a vibration inducing mechanism 402. A vibration detector 501 detects the induced vibrations in the cantilevered panel portion PCI and a similar optical vibration detector sensor 502 detects the vibrations induced in the cantilevered portion PC2. The panel position indicated P4 is at the out-flow side of the system and continues on through the conveyor system.

As can be seen from the foregoing, there is a continuous test system, suitable for on-line quality control signals from the temperature sensor, weigh station and vibration detectors being fed to suitable analyzers and computers to provide an indication of the quality of the manufactured panels.

Before reaching the torsion/bending vibration test station panels moving down a production line pass through a panel separation stage that introduces a space between successive panels. A panel entering the test station is first weighed while on a conveyor supported by a suitable weighing platform. Simultaneously the panels mean thickness and temperature at mid-length are determined from the series of measurements made by a pair of optical gauges located above and below the panel and an infrared thermometer. As the panel leaves the weighing stage it passes between the lateral guides before being clamped between the two pairs of rotary clamps that are spaced equidistantly from the mid-length of the panel. The horizontal distance separating the clamps is adjustable to allow for different test spans of the cantilevered portion of the panel. When the leading-edge on one side of the panel goes over the cam 401, which will induce the torsion/bending vibration, the latter moves downward until a preset position is reached at which point it remains stationary. When the trailing edge of the panel drops off the cam, the torsion and bending vibration are induced by the sudden release of the eccentric load. The complex vibration is then detected by the optical vibration sensor 501, under which is now located the leading edge of the panel. The vibration sensor is so designed as to be insensitive to the panel movement. When the opposite end of the panel reaches the adjustable cam 402, the aforementioned series of events repeat. The cam is adjustable vertically so as to selectively vary the amount of distortion of the panel. This allows for different panel thickness as well as amount of vibration induced. The panel weight, thickness, temperature, and mean frequencies in torsion and bending (for both sides of the panel) monitored by a computerized data acquisition system, are processed according to established relationships to yield the panels modulus of elasticity in bending and its shearing modulus of rigidity.

We claim:

1. A method for non-destructively testing the quality of a manufactured panel made of wood products comprising:
   a) supporting the panel in such a manner as to have a portion thereof projecting beyond the support and thereby providing an unsupported panel portion;
   b) causing complex vibrations in said unsupported portion of the panel so as to include both twisting and bending vibrations;
   c) sensing said complex vibrations and providing an output signal as a result thereof; and
   d) analyzing, from said output signal, each of the bending and twisting vibrations simultaneously induced into the panel and therefrom providing an indication of the quality of the panel by virtue respectively from an indication of its modulus of elasticity and shear modulus.

2. The method of claim 1 comprising clamping the panel at the support therefore whereby the unsupported panel portion is cantilevered outwardly.

3. The method of claim 2 comprising striking the panel with a blow at a position off-set from its axis of symmetry to thereby cause said complex vibrations in said panel.

4. The method of testing the quality of panels being manufactured in a mill comprising:
   a) locating on-line apparatus for the nondestructive testing of a panel;
   b) weighing a panel to be tested;
   c) clampingly engaging the panel such that a portion of the panel is cantilevered from the clamped portion thereof;
   d) causing complex vibrations to occur in the cantilevered portion of the panel so as to include both twisting and bending vibrations;
   e) sensing the complex vibrations and providing an out-put signal as a result thereof; and
   f) analyzing from said out-put signal, each of the bending and twisting vibrations induced into the panel and together with the mass information of the panel, determining from the panels modulus of elasticity and shear modulus, the quality of the panel being produced.

5. Apparatus for non-destructively testing the quality of manufactured panels made of wood products comprising:
   a) a bar-like clamp means for clampingly engaging and supporting a panel so as to have a portion of such panel cantilevered outwardly therefrom;
   b) means located at a position off-set from the axis of symmetry of the cantilevered portion of the panel for detecting complex vibrations induced into the cantilevered portion of the panel; and
   c) means for causing vibrations in said cantilevered portion of the panel including both bending and torsional vibrations.

6. Apparatus for non-destructively testing the quality of manufactured panels made of wood products comprising:
   a) a frame having a defined open area into and through which a panel can be fed endwise;
   b) a beam extending along an edge of said open area, said beam providing a clamping base that has a substantially smaller panel engaging area than the major surface area of the panel to be tested;
   c) bar-like means movably mounted to clampingly press a panel against said beam; and
   d) means located in selected spaced relation with respect to said beam, and at a position off-set from an axis of symmetry of a portion of a panel projecting in cantilever fashion from said beam, for detecting vibrations induced in the cantilevered portion of the panel and providing signals representative of bending and torsional vibrations in the panel that when analyzed, provide an indication of the quality of the panel.

7. The apparatus of claim 6 including pillow block means on the beam and bar-like member for engaging respectively oppose faces of the panel.

8. The apparatus of claim 6 including means for weighing the panel and means to determine the thickness of the panel.

9. Apparatus for non-destructively testing the quality of manufactured panels made of wood products comprising:
   a) a frame having at least one lower horizontal beam-like member on which a panel can rest;
   b) at least one upper horizontal beam-like member co-acting with said lower beam-like member to clampingly engage a panel therebetween, said panel having a portion projecting in cantilever fashion from where it is clampingly engaged,
   c) panel weighing means; and
   d) means for determining the thickness of the panel.

10. The apparatus of claim 9 wherein said upper and lower clamping means comprises a lower horizontally disposed beam fixed in position and an upper horizontal beam aligned therewith and movable toward and away therefrom.

11. The apparatus of claim 9 wherein said upper and lower clamping means comprises a pair of counter rotating endless belts.

12. The apparatus of claim 11 wherein at least one of said endless belts is driven to propel the panel endwise.

13. The apparatus of claim 9 including infeed and outfeed conveyor means for moving a panel endwise into and out of the panel clamping means.

14. Apparatus for use in testing the quality of wood panels comprising:
   (a) Conveyor means for moving panels one after another along a selected path;
   (b) a weigh station located in the path of the panels to weight a panel as it moves along said selected path;
   (c) means for clampingly engaging a central portion of a panel, as it moves along said path, at a location downstream of said weight station, said clamping engaging a portion only of the panel with remaining portions being cantilevered therefrom;

(d) means for inducing complex vibrations in said cantilevered portions of a panel projecting from the clamping means in a direction perpendicular to its direction of travel;

(e) means for detecting the induced vibrations in the panel as it moves along said path; and (f) means to analyze formation obtained from said vibration detection means.

15. Apparatus for use in testing the quality of wood panels comprising:

(a) a weigh station located in the path of panels moving by conveyor means along a selected path;

(b) means for clampingly engaging a central portion of the panel as it moves along said path downstream of the weigh station, said clamping engaging a portion only of the panel with remaining portions being cantilevered therefrom;

(c) means for inducing complex vibrations in the cantilevered portions of the panel projecting from the clamping means;

(d) means for detecting the induced vibrations in the panel as it moves along said path; and (e) means to analyze information obtained from the vibration detector means, the weigh means and the panel thickness detecting means to determine the modules of elasticity and shear modulus of the panel.

16. A method of improving the manufacture of wood panels in a mill comprising providing on-line panel quality detection that includes:

a) means to weigh a panel while moving;

b) means to determine the thickness of the panel;

c) means clampingly engaging a central portion of the panel as it moves along a selected path whereby the remaining portion is cantilevered respectively from each of opposite sides of a center portion of such path;

d) means to induce bending and twisting vibrations in at least one of the cantilevered portions of the panel, and e) means to detect the vibrations induced into the cantilevered panel portion and provide signals that can be analyzed to indicate respectively the modulus of elasticity and shear modulus of the panel.

17. Apparatus as defined in claim 6 wherein said beam and bar-like means are disposed horizontally.

18. Apparatus as defined in claim 16 wherein said beam is in a fixed location underlying said bar-like means and including movably mounted panel weighing means underlying a panel resting horizontally flat wise on said beam, said weighing means being selectively movable to raise the panel off the beam for weighing the same.

19. A system for testing the quality of a manufactured panel containing wood products comprising:

(a) a panel conveying means for moving a panel along a selected path;

(b) releasable elongate clamp means for temporarily clampingly engaging gand supporting a panel on said path to be tested nad in such manner that at least one portion of such panel is cantilevered from the clamp;

(c) signal means providing output signals representative of complex vibrations in the panel at a location offset from an axis of symmetry of the cantilevered panel portion; nad (d) means for processing said output signals providing an analysis of each of bending and twisting vibrations and therefore enabling determination of the quality of the panel.

* * * * *